(12) United States Patent
Dam-Huisman et al.

(10) Patent No.: US 12,721,974 B2
(45) Date of Patent: Sep. 1, 2026

(54) CANNULA TIP PROTECTOR

(71) Applicant: Crea IP B.V., Vierpolders (NL)

(72) Inventors: Adriaantje Coliene Dam-Huisman, Delfgauw (NL); Joep Hiemstra, Schiedam (NL)

(73) Assignee: Crea IP B.V., Vierpolders (NL)

( * ) Notice: Subject to any disclaimer, the term of this patent is extended or adjusted under 35 U.S.C. 154(b) by 428 days.

(21) Appl. No.: 18/562,860

(22) PCT Filed: May 25, 2022

(86) PCT No.: PCT/NL2022/050288
§ 371 (c)(1),
(2) Date: Nov. 21, 2023

(87) PCT Pub. No.: WO2022/250536
PCT Pub. Date: Dec. 1, 2022

(65) Prior Publication Data

US 2024/0207583 A1 Jun. 27, 2024

(30) Foreign Application Priority Data

May 25, 2021 (NL) ..................................... 2028279

(51) Int. Cl.
*A61M 25/06* (2006.01)

(52) U.S. Cl.
CPC ............................... *A61M 25/0625* (2013.01)

(58) Field of Classification Search
CPC ............ A61M 25/0625; A61M 5/3275; A61B 5/150656
See application file for complete search history.

(56) References Cited

U.S. PATENT DOCUMENTS

| | | | |
|---|---|---|---|
| 4,978,344 | A | 12/1990 | Dombrowski et al. |
| 2005/0033309 | A1 | 2/2005 | Ryan |

FOREIGN PATENT DOCUMENTS

| | | | |
|---|---|---|---|
| EP | 1159979 | A2 | 12/2001 |
| EP | 1430834 | A2 | 6/2004 |
| EP | 1430834 | A3 | 11/2005 |
| WO | 2015187629 | A1 | 12/2015 |

*Primary Examiner* — Imani N Hayman
(74) *Attorney, Agent, or Firm* — Ipsilon USA—NLO

(57) ABSTRACT

Provided herein is a cannula tip protector assembly for a Luer type syringe having a Luer connector with a syringe needle having a first diameter, and a needle tip having a second diameter smaller than the first diameter, the needle tip attached in fluid communication to the syringe needle at an end of the syringe needle opposite the Luer connector, a protection sleeve slidably positioned over the syringe needle and needle tip, and a cannula tip protector actuator unit having a Luer connector attachment part and a protection sleeve connector, the cannula tip protector actuator unit arranged to move the protection sleeve from a first position in which the needle tip is covered by the protection sleeve to a second position in which the needle tip is exposed outside the protection sleeve.

17 Claims, 3 Drawing Sheets

10
17
19
2
11
18
15
16
3
12
5
4

19
25
26
22
17
20
2
23
18
24
21
3
16
12
5
4

CANNULA TIP PROTECTOR

FIELD OF THE INVENTION

The present invention relates to a cannula tip protector assembly for a Luer type syringe comprising a Luer connector with a syringe needle having a first diameter, and a needle tip having a second diameter smaller than the first diameter, wherein the needle tip is attached in fluid communication to the syringe needle at an end of the syringe needle opposite the Luer connector, and a protection sleeve slidably positioned over the syringe needle and needle tip.

BACKGROUND ART

US patent publication US 2014/0128896 discloses a small gauge surgical instrument with a support device. The support device is a sleeve which can be shifted in and out from the instrument handle to provide support at various positions along the instrument flexible tip, or along a predetermined part of the instrument flexible tip.

European patent publication EP-A-1 955 684 discloses a surgical probe having a retractable reinforcing sleeve, able to be used in conjunction with a trocar cannula positioned in an eye. When the probe is inserted into the eye, through the trocar cannula, the trocar cannula becomes removably attached to the distal end of the sleeve, thus acting as a stiffening device. The sleeve is sliding back into the probe handle as the probe tip is advanced into the eye.

SUMMARY OF THE INVENTION

The present invention seeks to provide an improved cannula tip protector assembly for a Luer type syringe.

According to the present invention, a cannula tip protector assembly as defined above is provided, further comprising a cannula tip protector actuator unit, comprising a Luer connector attachment part and a protection sleeve connector, the cannula tip protector actuator unit being arranged to move the protection sleeve from a first position wherein the needle tip is covered by the protection sleeve to a second position wherein the needle tip is exposed outside the protection sleeve. These features may provide for an improved protection of the needle tip for safely and accurately performing e.g. a subretinal injection procedure.

SHORT DESCRIPTION OF DRAWINGS

Figures 1A, 1B:
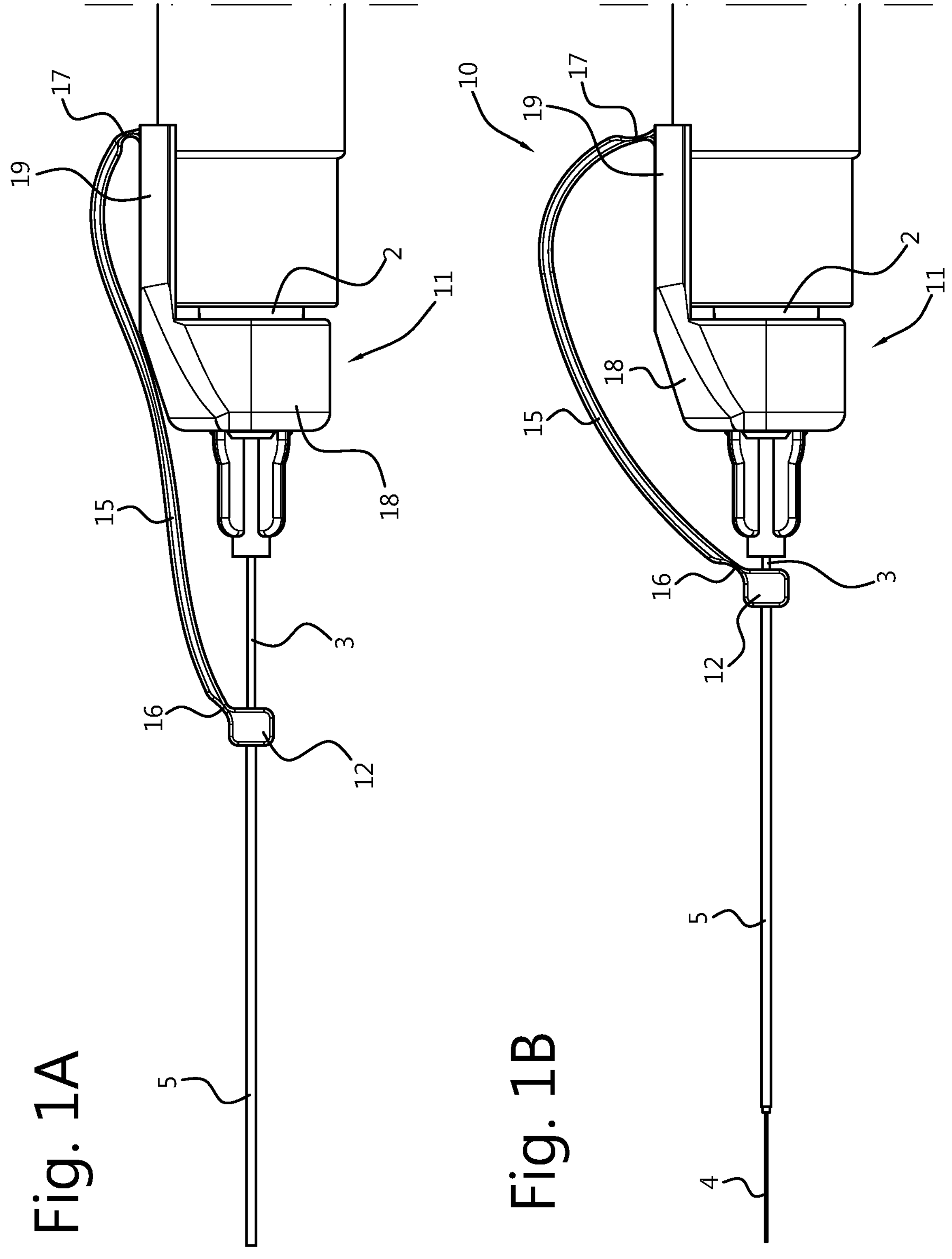
Figures 2A, 2B:
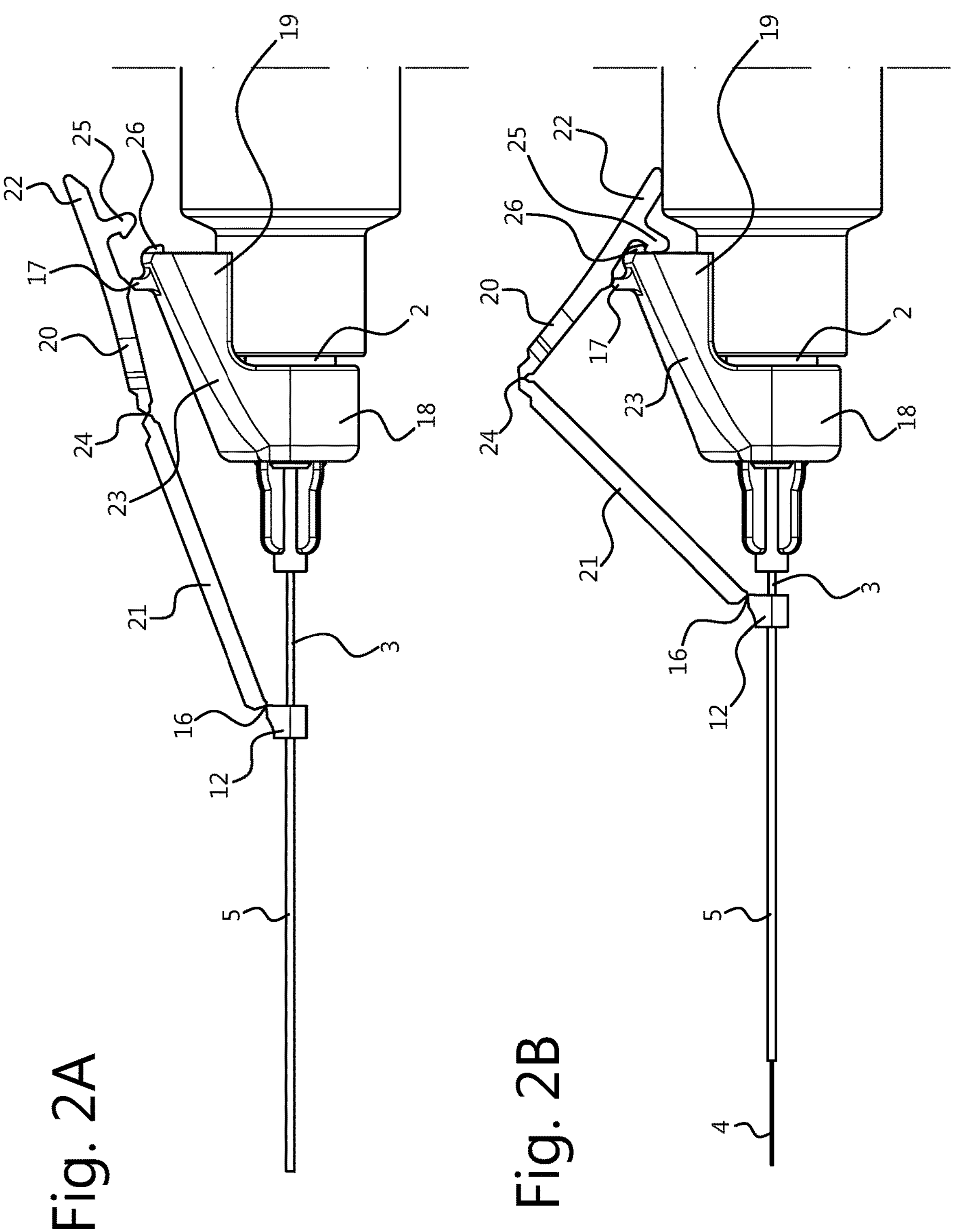
Figure 3A:
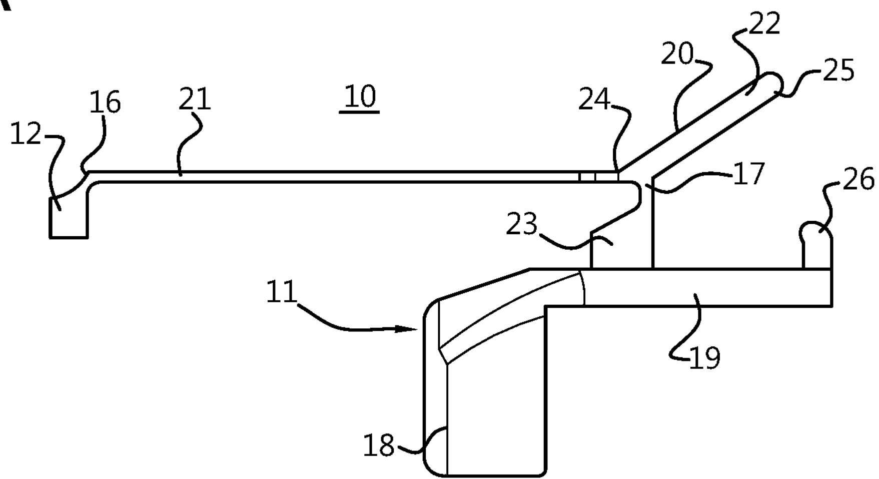
Figure 3B:
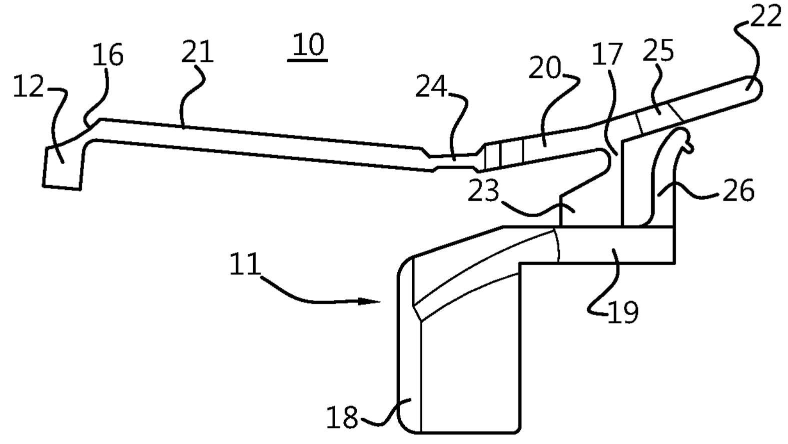
Figure 3C:
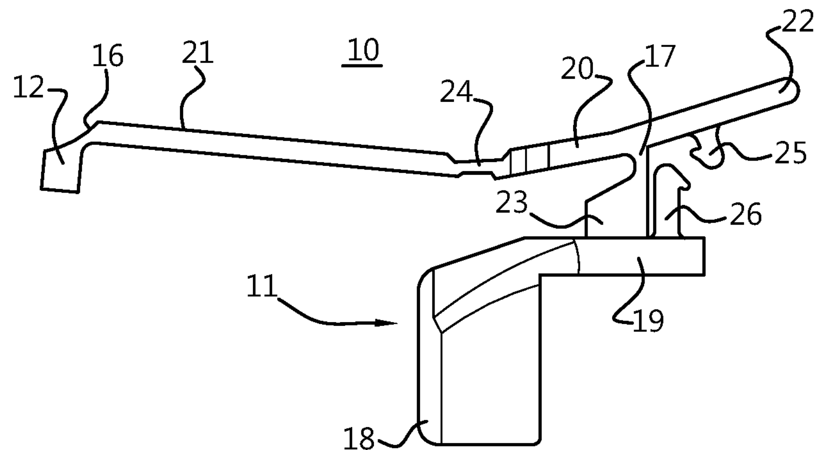

The present invention will be discussed in more detail below, with reference to the attached drawings, in which FIGS. 1A-B show a side view of a cannula tip protector assembly, according to an embodiment of the present invention;

FIGS. 2A-B show a side view of a cannula tip protector assembly, according to a further embodiment of the present invention, and FIGS. 3A-C show a side view of a cannula tip protector actuator unit, according to three exemplary embodiments of the present invention.

DESCRIPTION OF EMBODIMENTS

Subretinal injection is a procedure whereby fluid is delivered to an injection site at the back of an eye, generally in or behind the retina tissue, e.g. for drug or other substance delivery purposes. In such a procedure, a syringe having a needle (or syringe) with a thin tip is inserted into the eyeball (usually via a trocar), e.g. into the posterior chamber, whereby several layers of tissue are penetrated therethrough. Fluid is delivered through the tip of the needle to the injection site, using e.g. a conventional syringe arrangement.

Such a subretinal injection procedure requires steady handling to accurately penetrate through the eyeball and manipulate the fragile needle and tip therethrough to access the area behind the retina. However, to precisely and safely deliver fluid, the needle tip may have a very small diameter, and is susceptible to e.g. bending or breaking due to its fragility.

Thus, it would be desirable to provide improved instrumentation that may allow a user to accurately insert and penetrate the eyeball with a needle for delivery of fluid, yet, provide for sufficient protection thereof, thereby allowing the user to handle the syringe in a nice fashion to perform the subretinal injection procedure in a safe (and ergonomic) manner.

The present invention embodiments provide a cannula tip protector assembly for a Luer type syringe, providing improved protection of the needle for performing e.g. a subretinal injection procedure.

FIGS. 1A-B show a side view of a cannula tip protector assembly 1 for a Luer type syringe, according to an embodiment of the present invention. In the embodiment shown, the cannula tip protector assembly 1 comprises a Luer connector 2 with a syringe needle 3 having a first diameter, and a needle tip 4 having a second diameter smaller than the first diameter, wherein the needle tip 4 is attached in fluid communication to the syringe needle 3 at the syringe needle opposite the Luer connector 2. That is, as known the skilled person, at least a part of the needle tip 4 may be arranged within the syringe needle, wherein the syringe needle is in fluid communication with the Luer type syringe for delivery of the fluid through to the needle tip 4. The Luer connector 2 is arranged to connect to an end of the Luer type syringe.

In the embodiment shown in FIGS. 1A-B, the cannula tip protector assembly 1 further comprises a protection sleeve 5 slidably positioned over the syringe needle and needle tip 4. The protection sleeve 5 may cover at least a part of the syringe needle 3 and at least a part of the needle tip 4, i.e. cover an outer surface area thereof from (direct) exposure to an external environment.

The protection sleeve 5 has a length arranged to protect the syringe needle 3 and needle tip 4, wherein, as mentioned above, the syringe needle 3 and especially the needle tip 4 are susceptible to e.g. breaking or bending due to their fragility and small diameters. Thus, the protection sleeve 5 provides for proper protection of the syringe needle 3 and needle tip 4, yet, is also sufficiently strong to insert into and penetrate through an eyeball, or trocar present on the eyeball. The protection sleeve 5 may comprise any suitable material known to the skilled person, for example, a metal (e.g. stainless (surgical) steel or titanium), or (strong) plastic material.

Furthermore, in this embodiment (as shown in FIGS. 1A-B), the cannula tip protector assembly 1 further comprises a cannula tip protector actuator unit 10 comprising a Luer connector attachment part 11 and a protection sleeve connector 12, the cannula tip protector actuator unit 10 being arranged to move the protection sleeve 5 from a first position wherein the needle tip 4 is covered by the protection sleeve 5 to a second position wherein the needle tip 4 is exposed outside the protection sleeve 5, the first position being shown in FIG. 1A and the second position in FIG. 1B. The Luer connector attachment part 11 may be attached to a part of the Luer connector 2, and, the protection sleeve connector 12 may be attached to a part of the protection sleeve 5. It is noted that, in the first position, the needle tip 4 is fully covered by the protection sleeve 5.

The protection sleeve connector 12 may be connected to a part of the protection sleeve 5, and in several ways. For example, the protection sleeve 12 may be melted and/or glued onto the protection sleeve 5 for a strong connection thereof. Alternatively, the protection sleeve 12 may also comprise e.g. a ring-shaped element and threaded through the protection sleeve 5 in a tight manner (e.g. using friction for a secure connection thereof).

By keeping the Luer connector attachment part 11 fixed in position on the Luer connector 2 and moving the protection sleeve connector 12 in a direction towards the Luer connector 2 (e.g. by pulling it back), the protection sleeve 5 moves in-tandem from the first position to the second position, as shown in the FIGS. 1A-B embodiment. Thus, by using the cannula tip protector actuator unit 10, a user may choose to cover the needle tip 4 (i.e. the first position) by moving the protection sleeve 5 away from Luer connector 2, or choose to expose the needle tip 4 (i.e. the second position) by allowing the protection sleeve 5 to move towards the Luer connector 2. From this perspective, the needle tip 4 may be protected or exposed by the protection sleeve 5 as desired by the user.

In more general wording, the present invention embodiments, as described herein, relate to a cannula tip protector assembly 1 for a Luer type syringe, comprising a Luer connector with a syringe needle 3 having a first diameter, and a needle tip 4 having a second diameter smaller than the first diameter, wherein the needle tip 4 is attached in fluid communication to the syringe needle at an end of the syringe needle opposite the Luer connector 2. The cannula tip protector assembly 1 further comprises a protection sleeve 5 slidably positioned over the syringe needle and needle tip 4, and a cannula tip protector actuator unit 10 comprising a Luer connector attachment part 11 and a protection sleeve connector 12, the cannula tip protector actuator unit 10 being arranged to move the protection sleeve 5 from a first position wherein the needle tip 4 is covered by the protection sleeve 5 to a second position wherein the needle tip 4 is exposed outside the protection sleeve 5. This may provide an improved cannula tip protector assembly 1 for a Luer type syringe, providing for an improved protection of the needle tip 4 for safely and accurately performing e.g. a subretinal injection procedure.

A further possible advantage of the present invention embodiments is that the cannula tip protector assembly 1 is easily compatible with (and can be readily attached to) a wide range of Luer syringes of different sizes, for example, a standard 5 cc Luer syringe. In the same vein, an additional advantage is that the cannula tip protector assembly 1 is also compatible with syringe needles 3 and needle tips of varying diameter.

An even further advantage is the improved visualisation of the needle tip 4; owing to the larger diameter, the user is more easily able to view (via e.g. a camera) the protection sleeve 5 during the procedure, thereby allowing for accurate positioning thereof with respect to an injection site before exposing the needle tip 4 for fluid injection.

To detail the advantageous characteristics of the cannula tip protector assembly 1 in relation to the present invention embodiments described herein, the following non-limiting example is presented. The cannula tip protector assembly 1 is attached to a Luer type syringe via the Luer connector 2, wherein the Luer type syringe is provided with an control arrangement to inject (i.e. output) fluid held in the Luer type syringe upon actuation thereof, e.g. using a foot pedal. The Luer syringe is filled with fluid, and a needle tip 4 is attached to the end of the syringe needle 3 and in fluid communication therewith. During a procedure, initially the needle tip 4 is covered by the protection sleeve 5 (i.e. the first position) for protection thereof, and is e.g. inserted into a posterior chamber of an eyeball and through the retina. The (end of the) protection sleeve 5 is then accurately positioned with respect to an injection site (through the use of e.g. a camera) and accurately held in position. Using the cannula tip protector actuator unit 10, the protection sleeve 5 is actuated from the first position to the second position, thereby exposing the needle tip 4 to the injection site. The control arrangement may then be actuated via the foot pedal, and the fluid held in the Luer type syringe is injected through the needle tip 4 to the injection site. After retracting the needle tip 4 from the injection site, the protection sleeve 5 may then be actuated from the second position to the first position to re-protect the fragile needle tip 4, and withdrawn from the eyeball.

From this perspective, when being manipulated through the eyeball, the fragile needle tip 4 is protected by the protection sleeve 5 in the first position. The protection sleeve 5 is also more easily visible during the procedure, allowing for accurate positioning thereof, and may easily be actuated between the first position and second position to expose the needle tip 4 for injection of fluids therethrough. In this light, such a cannula tip protector assembly 1 is also compatible with a range of Luer syringes and needle tip 4 diameters, thereby providing an easy-to-use and cost- and protection-effective cannula tip protector assembly 1.

In an embodiment, the cannula tip protector actuator unit 10 further comprises a latching mechanism for holding the protection sleeve 5 in the second position. The latching mechanism may comprise any latching mechanism known to the skilled person as such, for which possible implementing embodiments thereof are discussed later. In general, the latching mechanism provides easy use of the cannula tip protector actuator unit 10, allowing the user to safely hold the protection sleeve 5 in the second position for performing e.g. a subretinal injection procedure in an better and safer manner.

To that end, in an further embodiment, the second position is a stable position. The stable position allows secure use of the combination of cannula tip protector assembly 1 and Luer type syringe, as the user may firmly hold the combination while the protection sleeve 5 is in the second position without any large concerns of instability. For example, in relation to the non-limiting example described above, the protection sleeve 5 is stably held in the second position to expose the needle tip 4 for injecting fluids therethrough, without large concerns of the protection sleeve 5 being unstable and e.g. accidently actuating to the first position.

In an exemplary embodiment shown in FIGS. 1A-B, the cannula tip protector actuator unit 10 further comprises an elongate resilient actuator part 15 connected to the protection sleeve connector 12 by a first hinge connection 16 and connected to the Luer connector attachment part 11 by a second hinge connection 17. The first and second hinge connections 16, 17 may comprise living hinge connections, providing for easy manufacturing of the cannula tip protector assembly 1.

As shown in FIG. 1B, the elongate resilient actuator part 15 may comprise an arcuate-like shape in 'rest' in the second position i.e. the rest position is a stable position. Upon actuation of the elongate resilient actuator part 15 in the 'rest' second position, via e.g. pressing a finger on a part thereof, there is a 'deformation' of the arcuate-like shape of the elongate resilient actuator part 15 (see FIG. 1A), and the protection sleeve 5 is actuated from second position to the first position.

In this manner, not only does the elongate resilient actuator part 15 provide for a simple connection between the Luer connector attachment part 11 and the protection sleeve connector 12, but also for simple and easy actuation of the protection sleeve 5 between the first position and second position.

With this in mind, in a further exemplary embodiment, the elongate resilient actuator part 15 has a length larger than a distance between the protection sleeve connector 12 and the Luer connector attachment part 11 in the second position, as shown in FIGS. 1A-B, where the distance is longer in the first position than in the second position. By having a length larger than the distance in the second position, this allows the elongate resilient actuator part 15 to have sufficient length to have an arcuate-like shape in the second position and to have a proper actuation of the protection sleeve 5 between the first position and second position.

In yet a further embodiment shown in FIGS. 1A-B, the Luer connector attachment part 11 comprises a Luer connection ring 18 and an actuation surface 19 extending away from the syringe needle, the second hinge connection 17 being positioned at an end part of the actuation surface 19 remote from the Luer connection ring 18. In this embodiment, the Luer connector 2 may be pushed or threaded through the Luer connection ring 18 for easy attachment thereof. Furthermore, in this embodiment, (one end of) the elongate resilient actuator part 15 is connected to the end part of the actuation surface 19 by the second hinge connection 17.

In the first position, as shown in FIG. 1A, the elongate resilient actuator part 15 is in contact with the surface of the Luer connection ring 18, thereby 'signalling' to the user that the needle tip 4 is covered and protected by the protection sleeve 5. In the second position, as shown in FIG. 1B, the elongate resilient actuator part 15 has an 'arcuate'-like shape in 'rest', thereby 'signalling' to the user that the needle tip 4 is exposed.

From this perspective, the presence of the Luer connection ring 18 and actuation surface 19 allows for easy use of the cannula tip protector actuator unit 10. The user may simply e.g. tap or press their finger on the 'arcuate'-like shape of the elongate resilient actuator part 15 in 'rest' to make (direct) contact with the Luer connection ring 18 for a proper actuation movement.

In this respect, the length of the actuation surface 19 is relevant for the use of the cannula tip protector assembly 1 with different Luer syringes; for example, a wider Luer syringe may involve a shorter actuation surface 19 for proper Luer connection, and vice versa.

Taking this into account, in an ever further embodiment, both the first and second positions are stable positions. This provides a bi-stable operation of the cannula tip protector actuator unit 10, allowing for even better stability during use of the cannula tip protector assembly 1. Again, in relation to the non-limiting example described above, the protection sleeve 5 may stably be held in the first position for handling and penetration into the eyeball, and, thereafter, actuated and stably held in the second position for injecting fluids through the exposed needle tip 4, and then re-actuated and stably held in the first position for withdrawal from the eyeball. This details the various advantages of having both the first and second positions as stable positions, and the skilled person would appreciate such advantages in stably and safely performing a careful and attentive movement in e.g. a subretinal injection procedure.

FIGS. 2A-B show a side view of the cannula tip protector assembly 1 for a Luer type syringe according to an embodiment of the present invention. Elements with the same function as in the exemplary embodiment shown in FIGS. 1A-B are indicated by the same reference numerals.

In the embodiment shown in FIGS. 2A-B, the cannula tip protector actuator unit 10 further comprises an articulated actuator part assembly 20, 21 connected to the protection sleeve connector 12 by a first hinge connection 16 and connected to the Luer connector attachment part 11 by a second hinge connection 17. The articulated actuator part assembly 20, 21 comprises parts connected by one or more joints for actuating the protection sleeve 5 between the first position and second position in a good, articulated manner, thereby allowing for simple and easy actuation of the protection sleeve 5.

In a further embodiment, the articulated actuator part assembly 20, 21 comprises a first straight arm 21 and a second straight arm 20 interconnected by a third hinge connection 24, the first straight arm 21 being connected to the protection sleeve connector 12 by the first living hinge connection 16 and the second straight arm 20 being connected to the Luer connector attachment part 11 by the second hinge connection 17, as shown in FIGS. 2A-B. Similar to the first and second hinges connections 17, 18 already described herein, the third hinge connection 24 may also comprise a living hinge connection. In this embodiment, the ends of the first straight arm 21 and second straight arm 20 are connected via the third hinge connection 24, as shown in FIGS. 2A-B.

As shown in FIG. 2A, in this embodiment, the first straight arm 21 and second straight arm 20 form an extended straight arm wherein the protection sleeve 5 is in the first position. As shown in FIG. 2B, in this embodiment, the first straight arm 21 and second straight arm 20 form a curved-like shape, e.g. a (substantially) V-shaped curvature wherein the protection sleeve 5 is in the second position, and wherein the third hinge connection 24 is the vertex of the curvature.

In this regard, the second straight arm 20 may comprise a finger support surface 22 arranged for assisted actuation of the protection sleeve 5, wherein the finger support surface 22 may be provided at e.g. an end of the second straight arm 20 opposite the third hinge connection 24.

Furthermore, in this embodiment and as shown in FIGS. 2A-B, the second straight arm 20 may be connected to the Luer connector attachment part 11 by the second hinge connection 17 via a connection tab 23. In other words, the Luer connector attachment part 11 comprises a connection tab 23 comprising the second hinge connection 17 for connection with the second straight arm 20.

All in all, the embodiment as shown in FIGS. 2A-B, with the articulated actuator part assembly 20, 21 comprising the first straight arm 21 and second straight arm 20 has a compact and efficient configuration of the (mechanical) parts, wherein the parts are nicely assembled together to form a suitable assembly, also with an aesthetically pleasing look, yet allow proper actuation of the protection sleeve 5 between the first position and second position.

In a specific embodiment shown in FIGS. 2A-B, and with reference to the embodiment described for the latching mechanism above, the latching mechanism comprises co-operating latch elements 25, 26 on the Luer connector attachment part 11 and on the second straight arm 20. As shown in the embodiments in FIGS. 2A-B, the co-operating latch elements 25, 26 may comprise a first latch element 25 provided on the second straight arm 20, e.g. near an end of the second straight arm 20 remote from the third hinge connection 24, and a second latch element 26 provided on the Luer connector attachment part 11. The first and second latch elements 25, 26 may both comprise a hook-type segment, as shown in FIGS. 2A-B.

By presence of the co-operating latch elements 25, 26, the user may easily hold the protection sleeve 5 in the second position with a proper and secure fastening means, yet, also easily allow the co-operating latch elements 25, 26 to unlatch for actuation of the protection sleeve 5 from the second position to the first position, by simply pressing on the third hinge connection 24.

Furthermore, in view of FIG. 2A, a user may easily e.g. press a finger down on the end of the second straight arm 20 (to subject a torque-like force on one side on second hinge connection 17) until the elements in the co-operating latch elements 25, 26 latch (and couple) onto one another for a secure fastening thereof, thereby actuating the protection sleeve 5 from the first position to the second position, wherein the protection sleeve 5 is held in the second position by the latching mechanism, as shown in FIG. 2B. To obtain that effect, the second straight arm 20 is rigid by design (by properly selecting material and dimensions) as to allow a force being exerted thereon on a point along its length.

In view of the above, the features mentioned above may be used to describe multiple, non-limiting embodiments of the latching mechanism, wherein several structures can be envisaged.

Accordingly, FIGS. 3A-C show a side view of the cannula tip protector actuator unit 10, according to three 'latching mechanism' embodiments of the present invention.

FIG. 3A shows a side view of the cannula tip protector actuator unit 10, with a 'spring'-like embodiment of the latching mechanism. In the 'spring'-like embodiment shown in FIG. 3A, the co-operating latch elements 25, 26 comprise a first latch element 25, wherein the first latch element 25 is an end part of the second straight arm 20 opposite the third hinge connection 24, and a second latch element 26 provided at an end part of the actuation surface 19 remote from the Luer connection ring 18, wherein the second latch element 26 comprises a hook-type segment. By pressing down on the end part of the second straight arm 20, i.e. the first latch element 25, the hook-type segment of the second latch element 26 may latch (and couple) onto the end of the second straight arm 20 for secure fastening thereof.

FIG. 3B shows a side view of the cannula tip protector actuator unit 10, according a 'hook-and-eye'-like embodiment of the latching mechanism. In the 'hook-and-eye'-like embodiment shown in FIG. 3B, the co-operating latch elements 25, 26 comprise a first latch element 25 provided in a part of the second straight arm 20, and a second latch element 26 provided at an end part of the actuation surface 19 remote from the Luer connection ring 18, wherein the first latch element 25 comprises an aperture, and the second latch element 26 comprises a hook-type segment. By pressing down on the end of the second straight arm 20, the hook-type segment of the second latch element 26 threads through the aperture of the first latch element 25, and may latch (and couple) onto a surface of the second straight arm 20 for secure fastening thereof.

FIG. 3C shows a side view of the cannula tip protector actuator unit 10, according a 'double hook'-like embodiment of the latching mechanism, similar to the FIG. 2A-B embodiment. In the 'double hook'-like embodiment shown in FIG. 3C, the co-operating latch elements 25, 26 comprise a first latch element 25 provided on a part of the second straight arm 20, and a second latch element 26 provided at an end part of the actuation surface 19 remote from the Luer connection ring 18, wherein both the first latch element 25 and second latch element 26 comprise a hook-type segment. By pressing down on the end of the second straight arm 20, the hook-type segments of the first and second latch elements 25, 26 may latch (and couple) onto one another for secure fastening thereof.

It is re-iterated that the embodiments described for the cannula tip protector actuator unit 10 (as shown in FIGS. 3A-C) are non-limiting examples, and alternative implementations of the features described therein are possible. For example, different co-operating latch elements 25, 26 (e.g. sliding and/or pin segments) may be envisaged.

As described herein, the length of the actuation surface 19 is relevant for use with different Luer type syringes. In this regard, it is noted the length of the actuation surface 19 shown the FIG. 3A embodiment is longer than those shown in the FIGS. 3B and 3C embodiments. Thus, the cannula tip protector actuator unit 10 shown in the FIG. 3A embodiment may be more suitable for a narrower (smaller volume) Luer type syringe, and the FIGS. 3B and 3C embodiments may be more suitable for a wider Luer type syringe.

In a specific embodiment, the needle tip 4 has a length of between 1 and 10 mm, providing good length to penetrate through e.g. the retina of the eye. In this sense, the distance between the first position and second position may also be between, for example, 1 and 10 mm.

In a further specific embodiment, the syringe needle has a length of between 1 and 5 cm, providing good length to reach e.g. the posterior chamber of the eye. In this sense, the syringe needle 3 may also, for example, have a length equal to or larger than the needle tip 4.

In an advantageous embodiment, the protection sleeve 5 has a diameter of 23G or less, e.g. 25G or even 27G. This may allow the protection sleeve 5 to be sufficiently strong and stiff for subretinal injection and other ophthalmic usage, and also able to withstand the forces and tolerances when e.g. inserting the protection sleeve 5 into the eyeball and resisting any bending thereof. Furthermore, such a diameter of 23G or less (25G or even 27G) is also suitable for use with a trocar, and causes less trauma than presently used larger gauge needles/sleeves.

In a further advantageous embodiment, the needle tip 4 has a diameter of 25G or less, e.g. 29G, or even 41G, providing a needle tip 4 specifically suited for e.g. a subretinal injection procedure, and thereby improving the usage thereof. In particular, a diameter of less than 29G e.g. 41G provides good capability for the delicate manipulation and guidance of the needle tip 4 during a subretinal injection procedure.

As an alternative, an embodiment is provided with a needle tip 4 diameter of 25G, e.g. in the form of a silicone tube attached to the syringe needle 3 with a diameter of 23G. In further embodiments, a syringe needle of 23G, 25G or 27G diameter can be provided with a needle tip 4 in the form of a silicone tube fitting inside the syringe needle 3 end. These embodiments are specifically suitable for back flush applications for removing fluid from the eye interior, also very close to delicate tissue such as the retina. The small dimensions and soft tip design lessen the risk for causing trauma of the nearby tissue. The silicone material needle tip 4 can be a straight tube variant, or a 'brush' type variant (as such known to the skilled person) to even further lessen the risk.

To perform such a subretinal injection procedure in even safer manner, in an even further advantageous embodiment, the needle tip 4 comprises a plastic material, e.g. PTFE. This may allow the needle tip 4 to be sufficiently small, yet, also be adequately strong for delivery of fluids therethrough. The needle tip 4 may comprise a plastic material comprising e.g. any medical grade material, for example, nylon, silicon or silicone rubber. In certain embodiments, the needle tip 4 may comprise a single material, i.e. made of a single plastic material.

In an embodiment, the cannula tip protector actuator unit 10 is a single component, e.g. an injection moulded element. Alternatively stated, for any one of the embodiments described herein, the (entire) cannula tip protector actuator unit 10 is formed using an injection moulding process to form a single component. Such an injection moulding process is not only efficient and capable of high reproducibility in providing a cannulate tip protector actuator unit 10 (i.e. it eases the manufacturing process), but also allows the features and (mechanical) parts thereof to be connected to form a one-piece component for easier and improved actuation thereof.

It is noted that any of the cannula tip protector actuator units 10 disclosed herein, such as the ones shown in FIGS. 1A-B, 2A-B and 3A-C, may also be provided as a separate component, and may be of use in any application domain, including a subretinal injection procedure, even without making use of the cannula tip protector assembly 1 as disclosed herein.

The present invention has been described above with reference to a number of exemplary embodiments as shown in the drawings. Modifications and alternative implementations of some parts or elements are possible, and are included in the scope of protection as defined in the appended claims.

The invention claimed is:

1. A cannula tip protector assembly for a Luer type syringe comprising a Luer connector with a syringe needle having a first diameter, and a needle tip having a second diameter smaller than the first diameter, wherein the needle tip is attached in fluid communication to the syringe needle at an end of the syringe needle opposite the Luer connector, a protection sleeve slidably positioned over the syringe needle and needle tip, and a cannula tip protector actuator unit comprising a Luer connector attachment part and a protection sleeve connector, the cannula tip protector actuator unit being arranged to move the protection sleeve from a first position wherein the needle tip is covered by the protection sleeve to a second position wherein the needle tip is exposed outside the protection sleeve.

2. The cannula tip protector assembly according to claim 1, wherein the cannula tip protector actuator unit further comprises a latching mechanism for holding the protection sleeve in the second position.

3. The cannula tip protector assembly according to claim 1, wherein the second position is a stable position.

4. The cannula tip protector assembly according to claim 3, wherein the cannula tip protector actuator unit further comprises an elongate resilient actuator part connected to the protection sleeve connector by a first hinge connection and connected to the Luer connector attachment part by a second hinge connection.

5. The cannula tip protector assembly according to claim 4, wherein the elongate resilient actuator part has a length larger than a distance between the protection sleeve connector and the Luer connector attachment part in the second position.

6. The cannula tip protector assembly according to claim 4, wherein the Luer connector attachment part comprises a Luer connection ring and an actuation surface extending away from the syringe needle, the second hinge connection being positioned at an end part of the actuation surface remote from the Luer connection ring.

7. The cannula tip protector assembly according to claim 1, wherein both the first and second positions are stable positions.

8. The cannula tip protector assembly according to claim 7, wherein the cannula tip protector actuator unit further comprises an articulated actuator part assembly connected to the protection sleeve connector by a first hinge connection and connected to the Luer connector attachment part by a second hinge connection.

9. The cannula tip protector assembly according to claim 8, wherein the articulated actuator part assembly comprises a first straight arm and a second straight arm interconnected by a third hinge connection, the first straight arm being connected to the protection sleeve connector by the first hinge connection and the second straight arm being connected to the Luer connector attachment part by the second hinge connection.

10. The cannula tip protector assembly according to claim 9, further comprising a latching mechanism that comprises co-operating latch elements on the Luer connector attachment part and on the second straight arm.

11. The cannula tip protector assembly according to claim 1, wherein the needle tip has a length of between 1 and 10 mm.

12. The cannula tip protector assembly according to claim 1, wherein the syringe needle has a length of between 1 and 5 cm.

13. The cannula tip protector assembly according to claim 1, wherein the protection sleeve has a diameter of 23G or less.

14. The cannula tip protector assembly according to claim 1, wherein the needle tip has a diameter of 25G or less.

15. The cannula tip protector assembly according to claim 1, wherein the needle tip comprises a plastic material.

16. The cannula tip protector assembly according to claim 1, wherein the cannula tip protector actuator unit is a single component.

17. The cannula tip protector assembly according to claim 1, wherein the cannula tip protector actuator unit is an injection molded element.

* * * * *